United States Patent
Shen et al.

(10) Patent No.: US 6,939,560 B2
(45) Date of Patent: Sep. 6, 2005

(54) PHARMACEUTICAL COMPOSITION HAVING TWO COATING LAYERS

(75) Inventors: Robert W. Shen, Kalamazoo, MI (US); Gerald A. Walter, Portage, MI (US)

(73) Assignee: Pharmacia & Upjohn Company, Kalamazoo, MI (US)

(*) Notice: Subject to any disclaimer, the term of this patent is extended or adjusted under 35 U.S.C. 154(b) by 0 days.

(21) Appl. No.: 09/738,333

(22) Filed: Dec. 15, 2000

(65) Prior Publication Data

US 2001/0000471 A1 Apr. 26, 2001

Related U.S. Application Data

(63) Continuation of application No. 09/139,449, filed on Aug. 25, 1998, now Pat. No. 6,228,397.
(60) Provisional application No. 60/057,216, filed on Aug. 29, 1997.

(51) Int. Cl.[7] .............................. A61K 9/28; A61K 9/32; A61K 9/36; A61K 9/42
(52) U.S. Cl. ........................ 424/441; 424/474; 424/480; 424/476; 424/482; 424/490; 424/497; 424/494; 424/495; 424/498
(58) Field of Search .................................. 424/441, 474, 424/480, 476, 482, 490, 497, 494, 495, 498, 475

(56) References Cited

U.S. PATENT DOCUMENTS

| | | | |
|---|---|---|---|
| 4,849,227 A | * | 7/1989 | Cho |
| 5,215,755 A | | 6/1993 | Roche et al. ................ 424/480 |
| 5,320,855 A | | 6/1994 | Roche et al. ................ 424/495 |
| 5,380,535 A | * | 1/1995 | Geyer et al. ................. 424/484 |
| 5,429,825 A | | 7/1995 | Reo et al. .................... 424/490 |
| 5,489,436 A | | 2/1996 | Hoy et al. .................... 424/441 |
| 5,891,476 A | | 4/1999 | Reo et al. .................... 424/498 |
| 6,228,397 B1 | * | 5/2001 | Shen et al. .................. 424/474 |

FOREIGN PATENT DOCUMENTS

| | | | |
|---|---|---|---|
| EP | 0 409 254 A1 | | 1/1991 |
| GB | 2 245 492 A | | 1/1992 |
| GB | 2245492 A | * | 8/1992 |
| JP | 116652 | | 5/1988 |
| WO | 94/08576 | | 4/1994 |

OTHER PUBLICATIONS

Remington's Pharmaceutical Sciences, 18th edition, pp1666–1669.*

* cited by examiner

Primary Examiner—James M. Spear
(74) Attorney, Agent, or Firm—Austin W. Zhang; Karen B. King

(57) ABSTRACT

The present invention provides a pharmaceutical composition which is substantially free of unpleasant tastes and orally administrable which comprises:

(a) an active medicament,
(b) an inner coating layer comprising an oil substance having a melting point at a range of from about 50° C. to about 100° C.,
(c) an outer coating layer comprising at least a polymeric substance.

8 Claims, No Drawings

PHARMACEUTICAL COMPOSITION HAVING TWO COATING LAYERS

CROSS-REFERENCE TO RELATED APPLICATIONS

This application is a continuation application of U.S. application Ser. No. 09/139,449, filed Aug. 25, 1998, now U.S. Pat. No. 6,228,397, which claims benefit of Provisional Patent Application No. 60/057,216, filed Aug. 29, 1997.

FIELD OF THE INVENTION

The present invention relates to an orally administrable pharmaceutical composition. More specifically, the present invention relates to a pharmaceutical composition comprising an active medicament with two coating layers which is substantially free of unpleasant tastes.

BACKGROUND OF THE INVENTION

Dimenhydrinate is a well-known therapeutic agent for the prevention or treatment of motion sickness. Like many drugs, however, in particular drugs containing amine or amido groups, it has a strong bitter taste. Without proper taste masking, dimenhydrinate and such drugs cannot be adapted into acceptable orally administrable forms, especially in the form of chewable tablets. Current taste masking techniques, including simple polymer coating of the drug substance, have not been entirely satisfactory for dimenhydrinate to achieve the desired degree of taste masking due to its appreciable solubility in both aqueous medium and various organic solvents. Therefore, solvents used in conventional coating processes often partially dissolve the drug and expose the drug substance on the surface of the preparation.

Recognizing the problems, the present invention is directed toward a taste-masking coating preparation for active medicaments which have the solubility profile as dimenhydrinate, i.e. the ability to dissolve in both organic solutions or aqueous medium in an appreciable extent. We have found that by using two appropriate coating layers such active medicaments can be substantially free from the unpleasant tastes.

INFORMATION DISCLOSURE

Abstract of Japanese Patent No. 116652 discloses the production of wax coated granulated pharmaceutical products using paraffins, beeswax, higher alcohols and/or fatty acid (esters).

The International Publication No. WO 94/08576 discloses a composition which is substantially free of the bitter taste associated with ranitidine and comprises a) a dispersion of lipid coated particles of ranitidine or a physiologically acceptable salt thereof in a non-aqueous vehicle, b) particles comprising ranitidine or a physiologically acceptable salt thereof incorporated into a core and coated with a lipid coating, and c) lipid coated particles of a form of ranitidine which is poorly soluble in water.

European Patent Application No. 0 409 254 A1 discloses a rapid-releasing oral particle pharmaceutical preparation with its unpleasant taste masked comprising a core and a film layer coating the core, the core at least containing a drug having an unpleasant taste and a water swelling agent, and the film layer at least containing ethylcellulose and a water-soluble substance.

SUMMARY OF THE INVENTION

One object of the present invention is to provide a pharmaceutical composition comprising an active medicament for oral administration, which is substantially free of unpleasant tastes associated with the active medicament.

A specific object of the present invention is to provide a pharmaceutical composition for oral administration which comprises an active medicament that is capable of being dissolved in both organic solutions or aqueous medium in an appreciable extent.

A further object of the present invention is to provide a pharmaceutical composition comprising an active medicament for oral administration in a form of chewable tablet, which has good taste, good appearance and suitable hardness.

The objects of the present invention have been accomplished in that the present invention provides a pharmaceutical composition that is substantially free of unpleasant tastes and orally administrable which comprises:

(a) an active medicament,
(b) an inner coating layer comprising an oil substance having a melting point at a range of from about 50° C. to about 100° C.,
(c) an outer coating layer comprising at least a polymeric substance.

DETAILED DESCRIPTION OF THE INVENTION

According to one aspect, the present invention provides a pharmaceutical composition which is substantially free of its bitter taste.

The present invention is formed from an active medicament having an inner coating layer and an outer coating layer. The active medicaments are of the ability to dissolve in both organic solutions or aqueous medium. However, while the composition of the present invention for such medicaments is its most important utility, they are applicable to all pharmaceutically active agents as well.

A suitable composition according to the present invention comprises an active medicament having an inner coating layer to form an inner core wherein the active medicament is in an amount of from about 5% to about 65% and the inner coating layer is in an amount of from about 95% to about 35% by weight of the entire inner core of the composition. The preferred inner core composition comprises an active medicament in an amount of about 50% and an inner coating layer in an amount of about 50% by weight of the entire inner core of the composition. The amount of active medicament in the composition is adjusted widely depending on the particular active medicament being used and the required concentration.

The oil substance useful in forming the inner layer of the composition includes a broad spectrum of pharmaceutically acceptable water-immiscible materials having a melting point at the range of from about 50° C. to about 100° C. such as hydrogenated vegetable or animal oil. For example, the oil substance can be hydrogenated or partially hydrogenated soybean oil, avocado oil, squalene oil, sesame oil, olive oil, canola oil, corn oil, rapeseed oil, safflower oil, sunflower oil, fish oils, flavored oils, water insoluble vitamins, or polyethylene glycol polymer having a melting point at least above 50° C., and mixtures thereof. The preferred oil for the inner coating layer is hydrogenated soybean oil.

The pharmaceutical composition of the present invention further comprises a polymer substance as an outer coating layer. Suitable pharmaceutically acceptable polymer substance for use in the outer coating layer includes cellulose based polymers such as alkylcelluloses, for example, methylcellulose, ethylcellulose or propylcellulose; hydroxyalkylcelluloses, for example, hydroxypropylcellulose or hydroxypropylmethylcellulose; and other cellulose based polymers, for example, cellulose acetate phthalate, hydroxypropyl methyl cellulose phthalate; and methacrylic acid copolymers; aminoalkyl methacrylate copolymers; methacrylic ester copolymers; glycerate triacetate; triethylcitrate; acetyl triethylcitrate; tributyl citrate; acetyl tributyl citrate; diethyl phthalate; dibutyl phthalate; or dibutyl sebacate. Particularly preferred polymeric substance is ethylcellulose, which may be any of the pharmaceutically acceptable ones, for example one having an ethoxyl content of 46.5 to 51% and having a viscosity of 4 to 100 cps. The outer coating layer may contain, in addition to polymeric substance, other pharmaceutical components such as suitable plastercizer, for example, propylene glycol or polyethlyene glycol polymer 400; or solvents, for example, ethanol, isopropyl alcohol, acetone or water. In general, the polymer substance is in an amount of from about 4% to 90% by weight of the total composition. The inner core is in an amount of from about 90% to about 4% by weight of the total composition and the other components are in the amount of from about 1% to about 40%. In a preferred composition of the present invention, the polymer substance is in an amount of from about 20% to about 40%, the inner core is in an amount from about 40% to about 70%, and the other composition is in an amount of from about 1% to about 5%.

If desired, the composition of the present invention may further comprise conventional pharmaceutical acceptable additives such as coloring agents, flavoring agents, fragrances, preserving agents, stabilizers, anti-oxidant and/or thickening agents.

The compositions according to the present invention may take the form of granules, tablets, pellets, pills, powders or capsules for oral administration. One important feature of the present invention is that the oil substance employed in the inner coating layer provides great flexibility; thereby the composition of the present invention is capable of being bent or flexed without damage during the tablet compressing process, and the medicine inside the oil coated beadlets will not leak out after chewing. As such, a chewable tablet is the particularly preferred dosage form of the present invention, which may be obtained by compressing the granules with a suitable chewable base such as sucrose, sorbitol, glucose, xylitol, mannitol or a mixture thereof.

The composition of the present invention may be prepared by known manufacturing techniques, for example, using a hot melt coating method to form an inner coating layer and then spray a suitable polymer solution on the inner core. The present invention will be better understood in connection with the following preparations and examples, which are intended as an illustration of and not a limitation upon the scope of the invention. Without further elaboration, it is believed that one skilled in the art can, using the preceding description and the information provided in the examples below, practice the present invention to its fullest extent.

| PREPARATION 1 Oil Coating the Inner Layer | |
| --- | --- |
| Dimenhydrinate | 5 Kg |
| Stearine Flake #17 (hydrogenated soybean oil) | 5 Kg |

To a stainless steel container, add Stearine Flakes and place the container on a hot plate. Apply heat to the hot plate to melt the flakes and maintain the batch temperature to about 80–85° C. To a Glatt GPCG 5, insulate the air supply unit (including the nozzle, nozzle wand and atomization air line). Atomization air is preheated to above 100° C. by using an air heater. Dimenhydrinate is added to the Glatt product container. Turn the turbine on by using cold air when the spraying system is hot. Spray the melted soybean oil on the dimenhydrinate and maintain the product temperature at about 48° C. by monitoring the spray rate until all of the soybean oil is used. Cool the batch to about 35° C. and then remove the product from Glatt product container. The product is screened through a #16 mesh screen.

| PREPARATION 2 Polymer Coating the Outer layer | |
| --- | --- |
| Stearine coated Dimenhydrinate (50% active ingredient) | 4 Kg |
| Ethylcellulose NF 4 cps | 2 Kg |
| Propylene Glycol USP | 220 g |
| Isopropyl Alcohol | 14 Kg |
| Acetone | 6 Kg |

To a suitable container add Isopropyl Alcohol, Acetone and the Propylene Glycol. While mixing slowly, add the Ethylcellulose into the above solvents and mix them until all of Ethylcellulose is dissolved. To the Glatt product container add the Stearine coated Dimenhydrinate. Spray the Ethylcellulose solution on to the batch according to the following parameters:

Product temperature: 24–27° C.

Exhaust temperature: 26° C.

Inlet temperature: 40° C.

Atomization air: 3 bar

Spray rate: 135 g/minute

The twice coated product is screened through a #16 mesh screen.

| PREPARATION 3 Chewable Tablet (Grape Flavored) | |
| --- | --- |
| Formula for 1,000 tablets | |
| Twice coated Dimenhydrinate (32.9% active ingredient) | 152.0 g |
| Manitol USP | 248.7 g |
| Sorbitol NF | 248.7 g |
| Malic Acid NF | 10.5 g |
| Aspartame NF | 7.0 g |
| Grape Flavor (spray dried, WL-261 | 20.0 g |
| FDC Red Lake #40 | 2.0 g |
| FDC Blue Lake #1 | 0.6 g |
| Magnesium Stearate NF | 10.5 g |

Add the above ingredients (without the Magnesium Stearate) into a Patterson-Kelley blender and mix for 30 minutes. Add the Magnesium Stearate and mix for 3 minutes. Compress the material into tablets using a tablet press with the weight of the tablets at 700 mg/tablet and tablet harness at 6–9 Strong Cobb Units.

Tablet hardness: 6–9 SCU
Friability: 0.2%
Taste: excellent taste with good color appearance

| EXAMPLE 1 | |
|---|---|
| A. Dimenhydrinate USP | 50% |
| Hydrogenated soybean oil | 50% |
| B. Ethylcellulose NF 4 cps | 32.15% |
| Oil coated Dimenhydrinate | 64.31% |
| Propylene Glycol | 3.53% |

We claim:

1. A pharmaceutical composition which is substantially free of unpleasant taste, comprising
granules comprising:
(a) an active medicament having an unpleasant taste, wherein the active medicament is capable of being dissolved in both organic solutions and aqueous media to an appreciable extent,
(b) an inner coating layer comprising an oil substance having a melting point at a range of from about 5° C. to about 100° C., wherein the inner coating layer and active medicament form an inner core, and
(c) an outer coating layer comprising a polymer substance,
wherein the active medicament is in an amount of from about 5% to about 65% by weight of the total inner core; the oil substance is in an amount of from about 35% to about 95% by weight of the total inner core; and the polymer substance is in an amount of from about 4% to about 90% by weight of the granules.

2. The pharmaceutical composition according to claim 1 wherein the oil substance is soybean oil, avocado oil, squalene oil, sesame oil, olive oil, canola oil, corn oil, rapeseed oil, safflower oil. sunflower oil, fish oils, flavored oils, water insoluble vitamins, polyethylene glycol polymer having a melting point of at least above 50° C. or mixtures thereof.

3. The pharmaceutical composition according to claim 1 wherein active medicament is in an amount of about 50% by weight of the total inner core.

4. The pharmaceutical composition according to claim 1 wherein the oil substance is in an amount of about 50% by weight of the total inner core.

5. The pharmaceutical composition according to claim 1 wherein the polymer substance is selected from the group consisting of: methylcellulose, ethylcellulose, propylcellulose, hydroxypropylcellulose, hydroxypropylmethylcellulose, cellulose acetate phthalate, methacrylic acid copolymers, aminoalkyl methacrylate copolymers, methacrylic ester copolymers, and glycerate triacetate.

6. The pharmaceutical composition according to claim 1 wherein the inner core is in an amount of about 90% to about 4% by weight of the total granule.

7. A chewable tablet which is substantially free of unpleasant taste comprising:
(i) a chewable base selected from the group consisting of sucrose, sorbitol, glucose, xylitol, mannitol or a mixture thereof, and
(ii) granules comprising:
(a) an active medicament having an unpleasant taste, wherein the active medicament is capable of being dissolved in both organic solutions and aqueous media to an appreciable extent
(b) an inner coating layer comprising an oil substance having a melting point at a range of from about 50° C. to about 100° C., wherein the inner coating layer and active medicament from an inner core, and
(c) an outer coating layer comprising a polymer substance,
wherein the granules are compressed with the chewable base, and wherein the active medicament does not leak out of the inner coating layer when the tablet is chewed.

8. The chewable tablet of claim 7, wherein the active medicament is in an amount of from about 5% to about 65% by weight of the total inner core; the oil substance is in an amount of from about 35% to about 95% by weight of the total inner core; and the polymer substance is in an amount of from about 4% to about 90% by weight of the total granules and is selected from the group consisting of methylcellulose, ethylcellulose, propylcellulose, hydroxypropylcellulose, hydroxypropylmethylcellulose, cellulose acetate phthalate, methacrylic acid copolymers, aminoalkyl methacrylate copolymers, methacrylic ester copolymers, and glycerate triacetate.

* * * * *

UNITED STATES PATENT AND TRADEMARK OFFICE
CERTIFICATE OF CORRECTION

PATENT NO. : 6,939,560 B2 Page 1 of 1
APPLICATION NO. : 09/738333
DATED : September 6, 2005
INVENTOR(S) : Robert W. Shen and Gerald A. Walter It is certified that error appears in the above-identified patent and that said Letters Patent is hereby corrected as shown below:

In the claims:

Claim 1 (b), Column 5 line 22 should read:
5<u>0</u>° instead of 5°

Signed and Sealed this

Twenty-eighth Day of November, 2006

JON W. DUDAS
*Director of the United States Patent and Trademark Office*